United States Patent
Peter

(10) Patent No.: US 6,175,610 B1
(45) Date of Patent: Jan. 16, 2001

(54) MEDICAL TECHNICAL SYSTEM CONTROLLED BY VISION-DETECTED OPERATOR ACTIVITY

(75) Inventor: Fritz Peter, Spardorf (DE)

(73) Assignee: Siemens Aktiengesellschaft, Munich (DE)

( * ) Notice: Under 35 U.S.C. 154(b), the term of this patent shall be extended for 0 days.

(21) Appl. No.: 09/245,869

(22) Filed: Feb. 8, 1999

(30) Foreign Application Priority Data

Feb. 11, 1998 (DE) ............................................... 198 05 529
Sep. 30, 1998 (DE) ............................................... 198 45 027

(51) Int. Cl.[7] ................................. G06F 3/00; G06K 9/62

(52) U.S. Cl. ............................... 378/8; 250/221; 345/166

(58) Field of Search .................... 378/8, 95; 345/435, 345/156, 166; 382/100; 250/221, 231.18

(56) References Cited

U.S. PATENT DOCUMENTS

| 4,843,568 | * | 6/1989 | Krueger et al. ........................ 382/100 |
| 5,325,473 | * | 6/1994 | Monroe et al. ........................ 345/429 |
| 5,703,356 |   | 12/1997 | Bidville et al. ....................... 250/221 |

FOREIGN PATENT DOCUMENTS

| 42 01 934 | 7/1993 | (DE) . |
| 196 12 949 | 8/1997 | (DE) . |

* cited by examiner

Primary Examiner—David V. Bruce
Assistant Examiner—Drew A. Dunn
(74) Attorney, Agent, or Firm—Schiff Hardin & Waite

(57) ABSTRACT

A medical system has at least one projection surface onto which a projection unit projects of operating elements. The system is controlled by detecting movements of a hand, preferably a finger, of an operator on the projection surface. An optical detector acquires the position and/or the motion of the finger relative to the projection surface, and a control unit evaluates the output data of the detector in order to control the system.

55 Claims, 5 Drawing Sheets

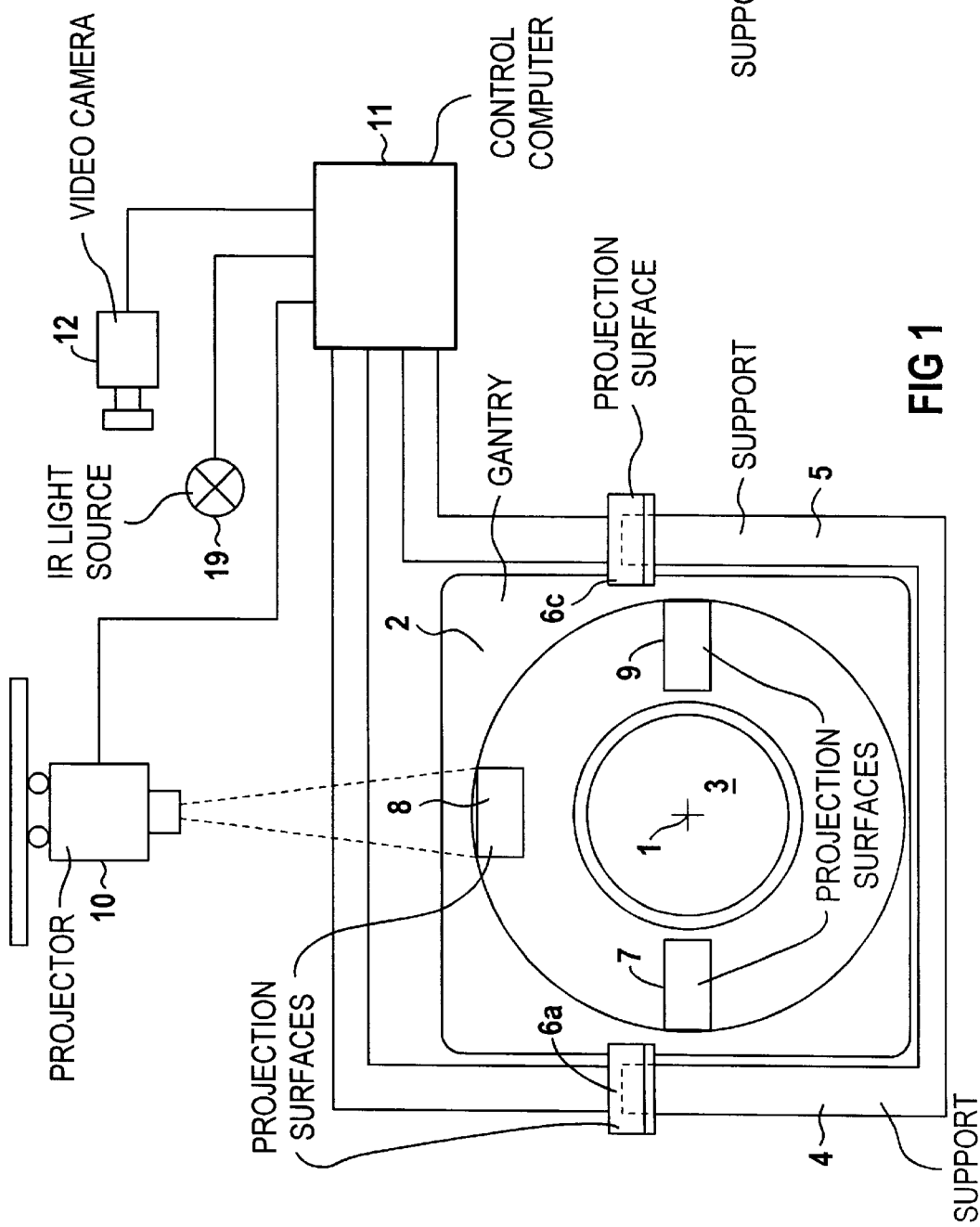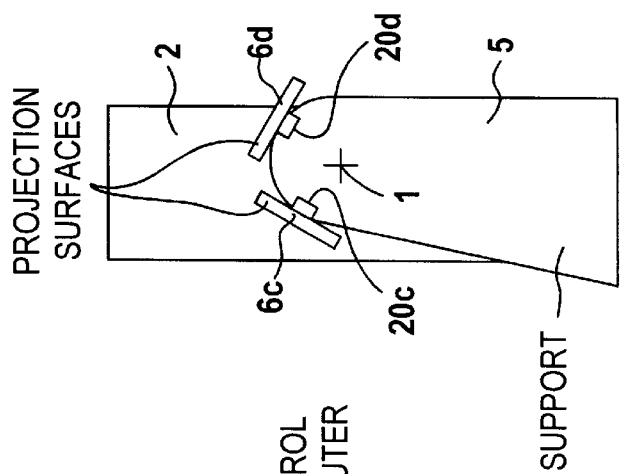

MEDICAL TECHNICAL SYSTEM CONTROLLED BY VISION-DETECTED OPERATOR ACTIVITY

BACKGROUND OF THE INVENTION

1. Field of the Invention

The present invention relates to a medical-technical system of the type having at least one operating element and a control means for controlling the system.

2. Description of the Prior Art

In such medical-technical systems, e.g. imaging systems or treatment systems, it is known to provide, as operating elements, keyboards or touch screens fashioned as video monitors. With the use of keyboards, disturbances or even defects often occur, due to the large number of electromechanical components that may be contained therein. With the use of touch screens, this problem is avoided, but due to the large dimensions of the video monitor it is often not possible to place the touch screen relative to an operator in such a way that a comfortable operation of the system is possible. In addition, with touch screens there is the danger of functional disturbances due to soiling.

German PS 196 12 949 discloses an input system having a projection surface to which a projector is allocated for the reproduction of operating elements in such a way that even in cases of medical application it is possible to control the system by the finger of an operator on the projection surface, the position and/or the motion of the finger relative to the projection surface being acquired by an optical detector, and the output data of the detector being used for controlling the system.

SUMMARY OF THE INVENTION

An object of the present invention is to provide a system of the type initially described wherein functionally reliable and comfortable operation is possible.

The above object is achieved in accordance with the principles of the present invention in a medical system wherein a projector projects, on a projection surface, images of at least one operating element for at least one system component. The projection surface has at least one surface structure, such as a raised portion or a recess, and the projector projects the image of the operating element onto this surface structure. A visual detector has a field of view which encompasses the projection surface, and detects the position and/or motion of an appendage of an operator on the projection surface. The detector generates a detector output dependent on the detected position and/or motion. The output of the detector is supplied to a control unit, which controls the system component dependent on the detected movement and/or position.

The appendage of the operator which is detected by the visual detector can be the operator's hand, and in particular a finger of the operator.

The invention can be considered as a virtual system, which does not require a video monitor as an input unit. The projection surface can be a smooth surface of the system that is already present anyway and is positioned conveniently relative to the operator. If no such surfaces are present, special projection surfaces can be provided that are preferably of plate-like construction and thus have a substantially smaller space requirement than do video monitors in the case of conventional touch screens. the invention therefore makes it possible to arrange the operating elements relative to an operator in such a way that comfortable operation is possible. At the same time, a high degree of reliability is provided, since electromagnetic components are not required.

Since the projection surface is provided with a recess and/or raised part in the region on which the projection unit projects an image of an operating element, the acquisition of the position of the finger on the projection surface is made easier. It is also possible for an operator to carry out reliable operation with only brief visual contact or entirely without visual contact, since due to the recess or raised part the operator is able to position his or her finger in such a way that an unambiguous allocation of the position to an operating element, and thus to an operating step, is possible.

In a further embodiment, operating element simulations (mock-ups) are provided that give an operator the feeling of being provided with conventional operating elements, e.g. keys, joysticks, and the like, without actually requiring electromechanical components. An identification of the operator action which is carried out thus can take place immediately by means of the control unit determining the position or motion of the operating element simulation by evaluating the output signals of the detector. Alternatively, the action identification can take place in a sequence wherein the control unit first determines the position or motion of the hand of the operator and only thereafter determines the position or motion of the operating element simulation from this hand motion. In both cases, the recognition and evaluation of these positions or motions is made easier because guidance of the hand or of the finger of the operator is provided by the operating element simulations.

In a version of the invention, the detector acquires the gestures of the operator, which can include determining the amplitude of the gestures. Additionally, or alternatively head motions of an operator and/or the expressions of an operator can be acquired. In all versions the control unit evaluates the gestures or the amplitude of the gestures and/or the head movements and/or the expressions, in order to control the system. To the extent that the gestures, head movements and expressions of an operator can be used to directly operate the medical system, it is the possible to carry out corresponding operating steps without requiring any operating elements, which can be particularly advantageous for the maintenance of sterile conditions.

In order to avoid an accidental occurrence of impermissible operating states, in a further version of the invention the control unit evaluates the position of the finger and/or the position of the operating element simulation and/or the gestures and/or the head movements and/or the expressions in order to check whether the execution of the corresponding operating steps could lead to an impermissible operating state. In the case of an impermissible operating state being found to be possible, the control unit does not enable the system to execute the "ordered" activity. A plausibility test, so to speak, thus takes place before the execution of operating steps.

In another embodiment of the invention, the system has several projection surfaces, and the reproduction of operating elements can optionally take place on several of these projection surfaces or on a single one of these projection surfaces, so that a variable arrangement of the operating elements, well-matched to the respective requirements, is possible.

In order to enable an arrangement of the projection surface relative to the operator that makes the operators work easier, in further embodiments of the invention at least one projection surface that can be oriented toward an operator is provided, or at least one projection surface that can be displaced relative to the system is provided.

If the medical system is an X-ray CT apparatus, it is particularly advantageous to attach projection surfaces to lateral supports for the gantry, since then a comfortable operation of the X-ray CT apparatus is possible, during examinations as well as during interventions, e.g. biopsies.

DESCRIPTION OF THE DRAWINGS

FIG. 1 is an end view of a medical system, in the form of a CT apparatus, constructed and operating in accordance with the principles of the present invention, connected to control components shown in a schematic block diagram.

FIG. 2 is a side view of a portion of the medical system of FIG. 1.

DESCRIPTION OF THE PREFERRED EMBODIMENTS

Figure 3:
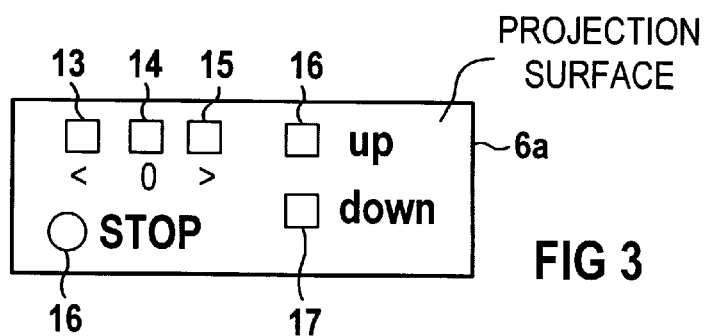
FIGS. 3 to 6 respectively show examples of displays produced on projection surfaces of the system according to FIGS. 1 and 2.

FIGS. 1 and 2 show an inventive medical system in the form of an imaging system—here, an X-ray CT apparatus which, except for the operator control arrangement in accordance with the invention, is constructed and operates in a known manner. This system includes a gantry 2 mounted so as to be tiltable around a horizontal axis 1. The gantry 2 is supported on the floor of the examination room by a stand, and has a measurement opening 3.

The stand has two supports 4, 5 that support the gantry 2.

On the front and back sides of the support 4, projection surfaces 6a and 6b are provided. Projection surfaces 6c and 6d are provided on the other support 5. A projection unit (in the case of the specified embodiment, a video projector 10), for example, is suspended on the ceiling of the examination room can direct a projected beam onto any of the projection surfaces 6a, 6b, 6c, 6d, 7, 8 or 9. The video projector 10 is connected to a control unit in the form of a control computer 11, and projects images of operating elements, stored in the control computer 11, onto at least one of the projection surfaces 6a to 6d, 7, 8 or 9. Only the projection surfaces 6a, 6c and 6d are visible in FIGS. 1 and 2, projection surface 6b being disposed on the support 4 at the same position as the projection surface 6d is disposed on the support 5. Moreover, in the control computer 11 operating steps corresponding to the individual operating elements are stored. The representation on the respective projection surfaces 6a to 6d, 7, 8 or 9 preferably corresponds to the representation that results/would result as a display screen surface given representation of the same information on a monitor connected to the control computer 11.

In addition, a detector (a video camera 12 in the specified embodiment) is connected to the control computer 11, which has a field of view encompassing at least that surface or surfaces 6a to 6d, 7, 8 or 9 onto which the video projector 10 is currently projecting operating elements.

The control computer 11 analyzes the output signal of the video camera 12 to determine whether the hand (in the case of the specified embodiment, the finger) of an operator is located on the respective projection surface (for example, the projection surface 6a shown in FIG. 3) on which operating elements in the form of keys 13 to 18 with associated labeling are being projected using the video projector 10. If this is the case, the control computer 11 interprets displacements of the finger of the operator on this projection surface as a motion with the mouse of a PC; it interprets the finger's remaining in place on one of the operating elements 13 to 18 for a determined time period, e.g. 1 second, as a mouse click. The control computer 11 then carries out the actuation of the operating step corresponding to the respective operating element.

The video projector 10, the video camera 12 and the projection surfaces 6a to 6d, 7, 8 and 9 together with the control computer 11, represent an arrangement that can be considered a virtual touch screen, because, as in an actual touch screen, the operator's finger can trigger interactions, namely operational steps.

In order to avoid errors in functioning, the video camera 12 is not sensitive to ambient light, but is only sensitive to a defined light spectrum, which makes possible an illumination of the projection surface to be monitored with a corresponding light source, so that the video camera 12 can recognize the finger of the operator. In the case of the specified embodiment, a video camera 12 sensitive only to infrared light and an infrared light source 19 are used.

An apparatus suitable for use as a movement signal analyzer in the inventive medical system is marketed by Siemens AG under the designation "SIVIT®-Siemens Virtual Touchscreen."

Figure 4:
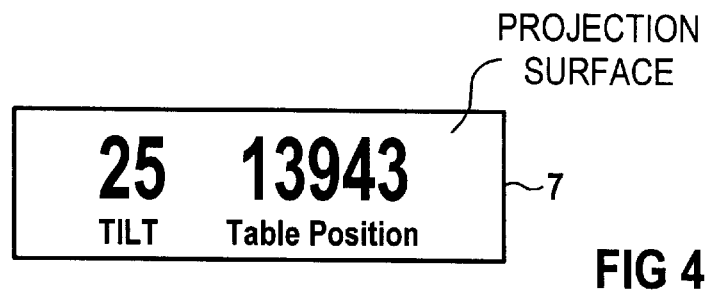
Figure 5:
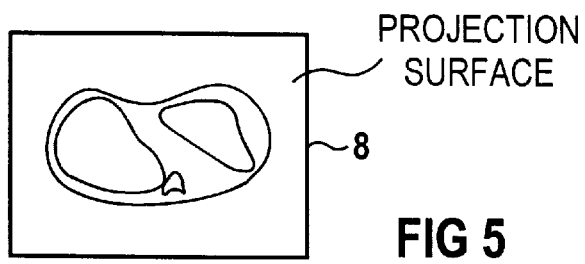
Figure 6:
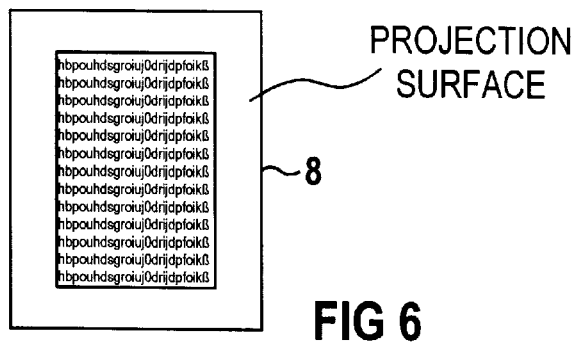

As FIGS. 4 to 6 show, with the video projector 10 displays of operating data of the medical-technical system can be shown on the further projection surfaces 7 to 9 provided on the gantry 2, e.g. the tilt angle of the gantry 2 and the position of a patient positioning table (FIG. 3) not shown in FIGS. 1 and 2, an image of a patient (FIG. 5) recorded using the CT apparatus, or alphanumeric character sequences (FIG. 6), e.g. patient data.

If the video camera 12 has a field of view encompassing not only the finger of the operator, but also at least the head of the operator, it is possible (as is the case for the specified embodiment for the projection surfaces 6a to 6d), using motor-driven displacement journals 20a to 20d that are controlled using the control computer 11 (only the displacement journals 20b and 20d are shown in FIGS. 1 and 2), to orient the camera 12 to the head of the operator in such a way that the operator can optimally perceive the respective projection surface 6a to 6d. This takes place by the control computer 11 evaluating the output signals of the video camera 12 in order to find out where the head of the operator is located.

Analogously, it is possible, using a motor-driven displacement journal (not shown) that is controlled by the control computer 11, to orient the video projector 10 onto the respective projection surface or surfaces 6a to 6d and/or 7 to 9 that is/are optimally reachable or optimally visible for the operator.

The orientation of the video projector 10 to the projection surfaces 6a to 6d and/or 7 to 9, as well as the orientation of the projection surfaces 6a to 6d to an operator, can also take place manually.

If a projection is supposed to take place simultaneously onto several projection surfaces 6a to 6d, this can be accomplished by a beam splitter (beam divider) allocated to the video projector 10. In addition, it is possible to provide several video projectors 10, in a manner not shown.

Figure 7:
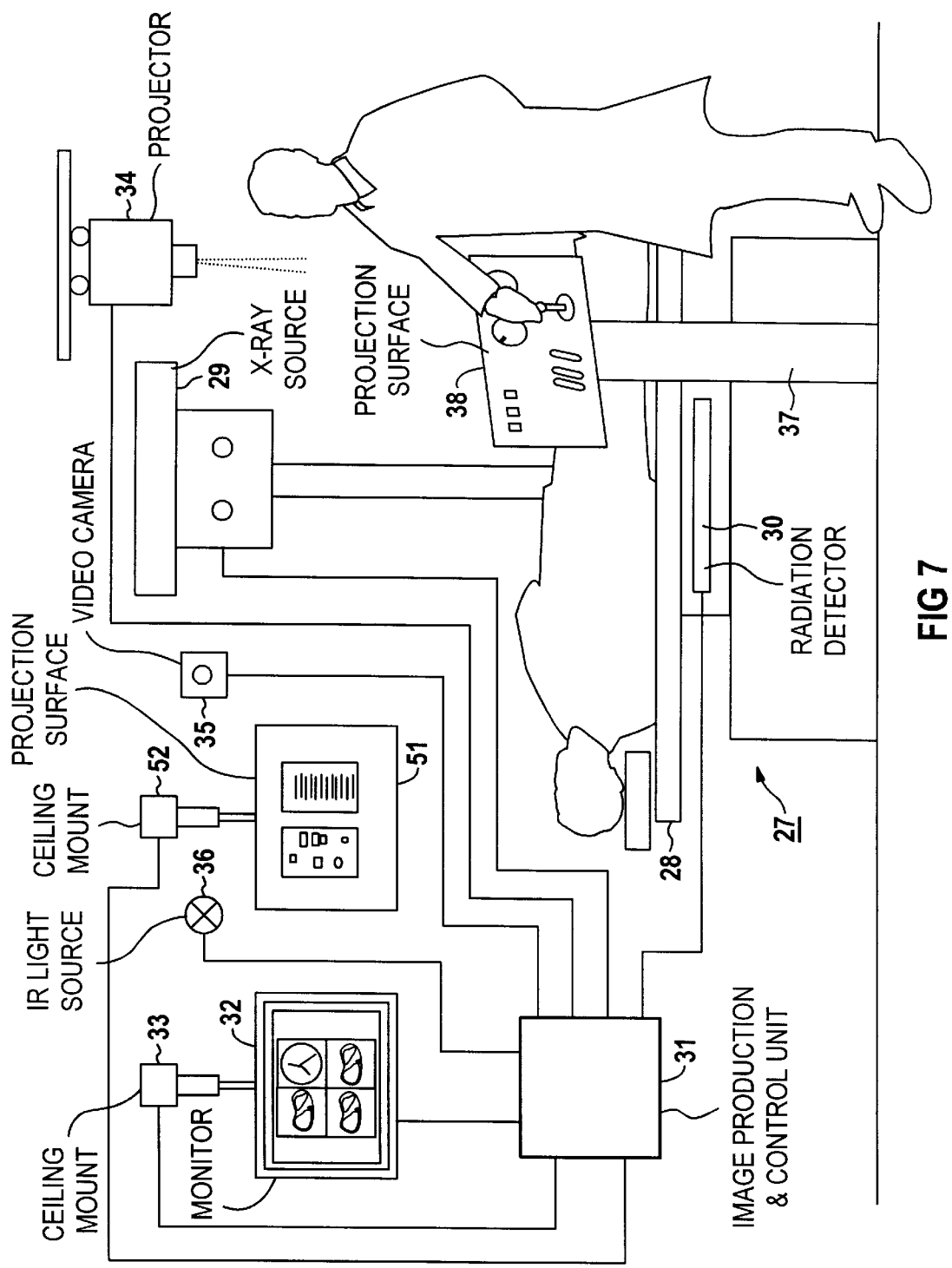
FIG. 7 shows a further embodiment of the inventive medical system.
Figure 8:
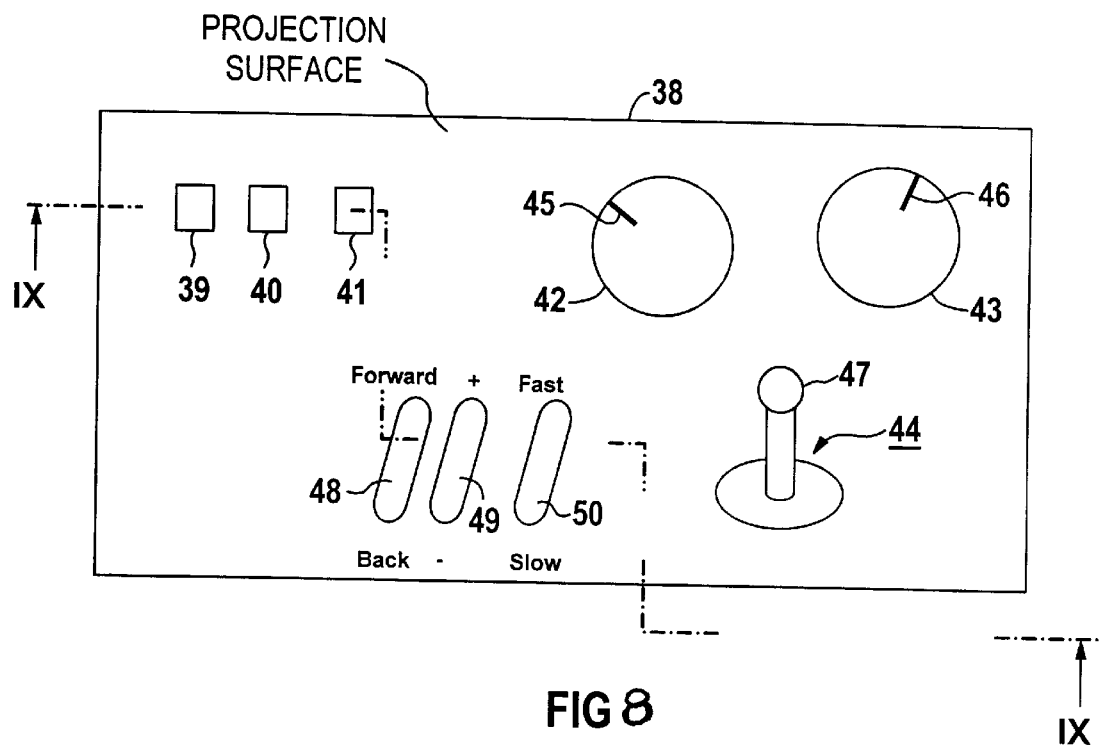
FIG. 8 shows a projection surface of the system according to FIG. 7 with the display effected thereon.

The medical-technical system according to FIGS. 7 and 8 is an X-ray diagnostic system with a patient positioning table designated 27 as a whole, having a positioning slab 28 on which a patient can be positioned in a lying position. Above the positioning slab 28 there is an X-ray source 29, which, together with a radiation detector 30 located under the positioning slab 28, e.g. a planar image detector, serves to produce X-ray shadowgraphs of a patient lying on the positioning slab 28.

The X-ray source 29 and the radiation detector 30 are connected to an image production and control unit 31 that represents the recorded X-ray shadowgraphs on a monitor 32, which in the specified embodiment is attached to a ceiling mount 33.

As in the case of the previously specified embodiment, a video projector 34, a video camera 35 and an infrared light source 36 are again provided, which, together with a projection surface 38 attached to a stand 37, enable the operation of the X-ray diagnostic system.

Figure 9:
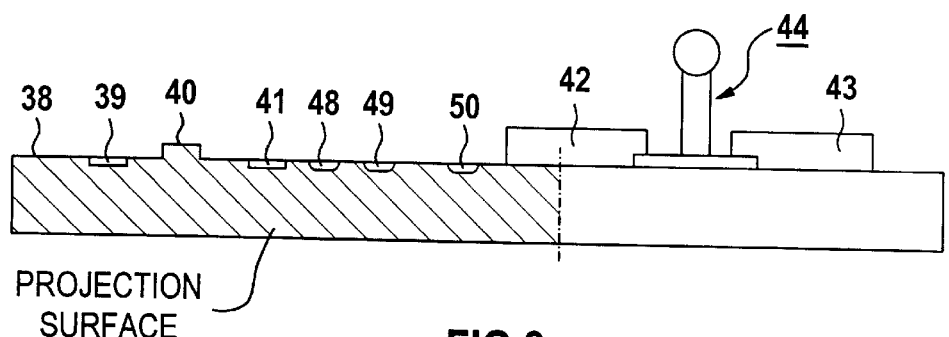
FIG. 9 shows an enlarged view of a section along the line IX—IX in FIG. 8.

As can be seen from FIGS. 8 and 9, the projection surface 38 is not only provided in order to enable operating elements, namely keys 39 to 41, to be projected onto it. Additionally, the projection surface 38 is provided with operating element simulations (mock-ups), namely two rotating knob simulations 42 and 43 and a joystick simulation 44.

The keys 39 to 41 serve for the operation of the X-ray diagnostic system in the manner explained in connection with the previously specified embodiment.

The rotating knob simulations 42 and 43 are provided, like real rotating knobs, with index marks 45 and 46, so that the image production and control unit can detect the positions of the rotating knob simulations 42 and 43 on the basis of the output signals of the video camera, and can convert them into corresponding operating steps. Monitoring of the position of the rotating knob simulations 42 and 43 takes place only when the image production and control unit 31 recognizes, on the basis of the output signals of the video camera 35, that the rotating knob simulations 42 and/or 43 have been actuated by an operator.

The position of the joystick simulation 44 is detected by the image production and control unit 31 from the position of the end piece (ball-shaped in the specified embodiment) 47 of the joystick lever, which accordingly must not be concealed by an operator during the actuation of the joystick simulation 44. The detection of the position of the joystick simulation 44 preferably takes place only when the image production and control unit 31 recognizes, on the basis of the output signals of the video camera 35, that an operator is actuating the joystick simulation 44.

Alternatively, or in addition, the image production and control unit 31 analyzes the operating processes carried out using the rotating knob simulations 42 and 43, as well as the joystick simulation 44, by, in the manner of a known gesture control unit, evaluating the hand motions and/or hand positions or finger motions and/or finger positions of the operator. The reliability of the recognition of these motions or positions is made easier by the guidance provided by the operating element simulations, i.e. the rotating knob simulations 42 and 43, as well as the joystick simulations 44; i.e. no arbitrary motions can take place.

In addition to the keys 39 to 41, on the projection surface 24 finger troughs 48 to 50 are additionally provided, labeled with printing or the like according to their respective function. These troughs 48 to 50 likewise serve to trigger operating steps, and correspond in their functioning to slider controls. If an operator places a finger in one of the finger troughs 48 to 50, the image production and control unit 31 determines, from the data corresponding to the output signals of the video camera 35, the finger position in the finger trough 48 to 50, and converts this into a corresponding operating step.

The ability to evaluate the finger position and finger motion by machine vision is also made easier by the finger troughs 48 to 50, since a defined positioning or direction of motion of the finger is predetermined.

Recesses or raised parts can also be provided in the region of projected keys, as is clear from FIG. 9 in connection with keys 39 to 41.

While the operating elements, i.e. the rotating knob simulations 42 and 43, as well as the joystick simulation 44, preferably serve for the setting of "analog" values, as do the finger troughs 48 to 50, the keys 39 to 41 preferably serve for the setting of binary values.

In addition to the projection surface 38, a further projection surface 51 is provided that serves for the display of graphic or alphanumeric information stored in the image production and control unit 31 or of images obtained using the X-ray diagnostic system, which the video projector 34 projects onto this projection surface 51.

Like the monitor 32, the projection surface 51 is attached to a ceiling mount 52. The ceiling mounts 33 and 52 can be displaced three-dimensionally with motors, in a manner not shown in more detail, these displacement motions being controlled by the image production and control unit 31.

For controlling the displacement motions of the ceiling mounts 33 and 52, the image production and control unit 31 analyzes, in the manner of a gesture controlling, the output signals of the video camera 35 with respect to the arm and head gestures of the respective operator. In this way, the image production and control unit 31 determines, based on the direction of motion, whether the monitor 32 or the projection surface 51 should be displaced. By evaluating the arm gestures, the image production and control unit 31 determines whether the monitor 32 or the projection surface 51 should be lowered or raised, moved to the left or to the right, or should be moved further from or closer to the operator. The image production and control unit 31 can evaluate the amplitude of the gestures in order to enable setting of the amplitude of the corresponding motions of the monitor 31 or of the projection surface 51.

Finally, the evaluation of the finger position specified in connection with the finger troughs 48 to 50 also represents a type of gesture controlling. Instead of slider controls, rotating knobs can also be realized by means of gesture controlling, namely in that rotatory motions of a hand or of a finger of an operator can be acquired and evaluated.

In the embodiment according to FIGS. 7 to 9, there also takes place an evaluation of the expressions of the operator, in order to modify the zoom factor with which images are displayed on the monitor 32. For this purpose, the image production and control unit 31 evaluates the output signals of the video camera 35 in order to determine whether the operator is displaying a smiling, normal, or grim facial expression. While in the case of a normal facial expression the zoom factor remains unchanged, or a displacement of the zoom factor currently in effect is terminated, in the case of a smiling facial expression a reduction of the zoom factor occurs, and in the case of a grim facial expression an increase of the zoom factor occurs.

Figure 10:
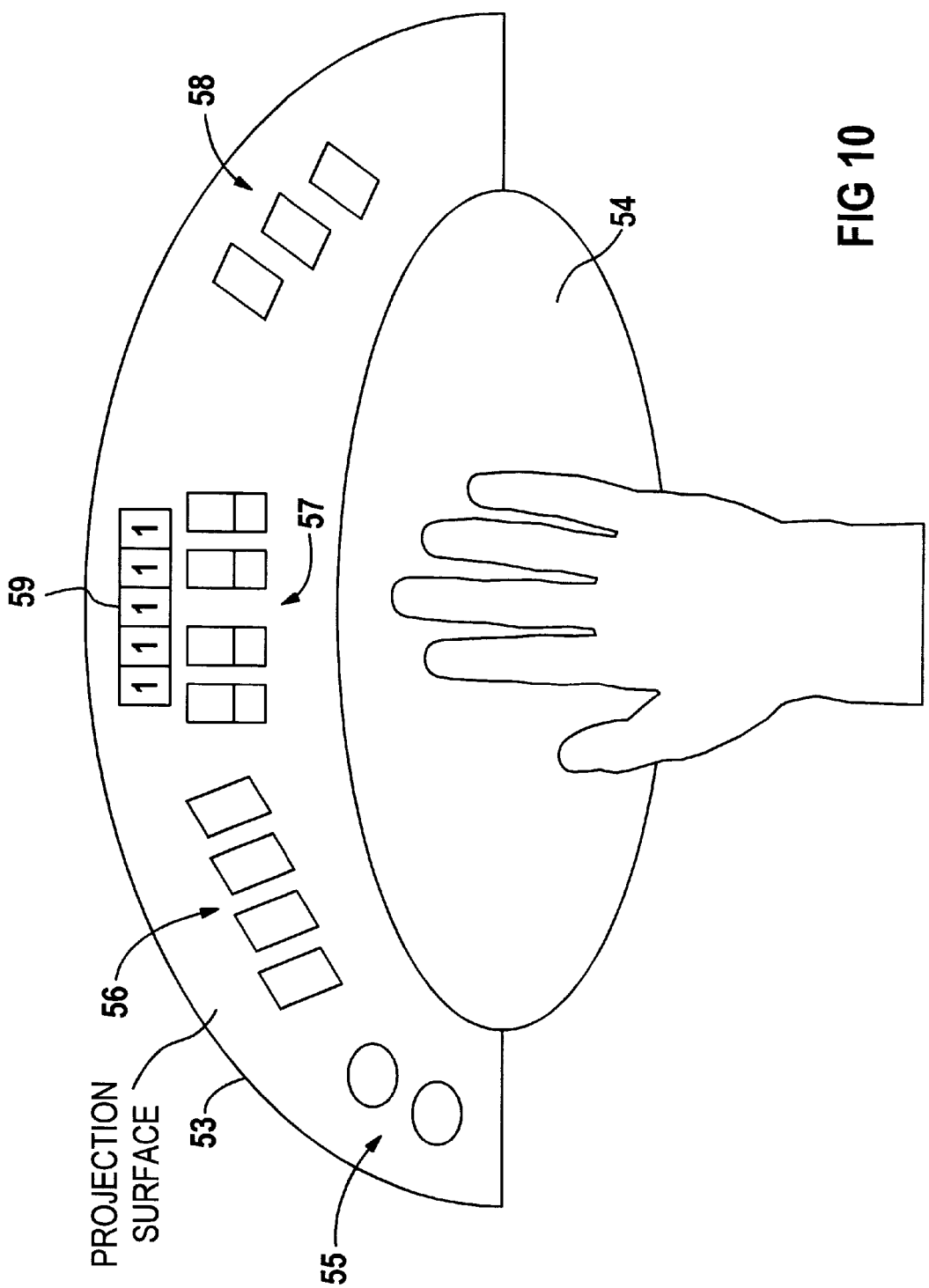
FIG. 10 shows a further example of a projection surface of an inventive system.

FIG. 10 shows, as an example, a projection surface 53 that is advantageous due to its ergonomically convenient construction and that can be used in inventive systems. The projection surface 53 has a hand rest 54 around which four groups of keys 55 to 58, as well as a numerical display field 59, are arranged in an easily reachable arrangement.

The invention is specified above for the example of X-ray apparatuses, namely an X-ray CT apparatus and a conventional X-ray apparatus. It can also be used in other medical imaging systems, e.g. magnetic resonance (MR) apparatuses or ultrasound apparatuses.

However, the application of the invention is not limited to medical imaging systems. Rather, it can also be used in medical therapy apparatuses, as well as in combinations of therapy apparatuses and imaging systems and in arbitrary other medical systems.

The type of operating elements projected in the case of the specified embodiment is to be understood merely as an example. This is also true for the types of operating element simulations, finger troughs, and raised parts and recesses specified in connection with the embodiments.

The type of information otherwise displayed on the projection surfaces in the case of the specified embodiments is also to be understood only as an example.

Likewise, the gestures, head movements, and expressions specified in connection with the embodiments and evaluated for operation are to be understood only as examples.

The projection surfaces need not necessarily be, as in the case of the specified embodiments, smooth or flat; in the case of interventions in particular it is also possible to use the patient's sheet as a projection surface.

In the case of both embodiments, the control computer 11 or the image production and control unit 31 checks the intended operating steps to determine whether they could lead to an impermissible operating state of the respective imaging system, and enables execution of the operating steps only if the occurrence of an impermissible operating state is excluded.

In sum, the basic advantages of the invention are as follows:

Both by modifying the projected operating elements and also by modifying the projected information, it is very easily possible to provide a human-machine interface constructed according to the respective current application of the system.

It is possible, by means of an application-specific projection, to reduce the number of operating elements offered to an operator by not projecting operating elements which are not required for the current application, and thus to simplify the operation of the imaging system.

Examinations or interventions with constant visual contact with the patient are made easier.

Expensive video monitors are replaced by simple, easily readable projection fields.

The preferably smooth projection surfaces can easily be kept sterile; in the interest of sterility, orientation of the projection fields by hand can be omitted.

Considerable savings in costs are possible in comparison with imaging systems that use conventional keyboards and monitors.

The invention creates the precondition of unifying the human-machine interfaces of a wide variety of medical-technical systems in a simple manner.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical system comprising:

a plurality of controllable system components;

a projection surface;

a projector which projects an image of at least one operating element for at least one of said system components onto said projection surface;

said projection surface having at least one surface structure and said projector projecting said at least one image of an operating element onto said at least one surface structure;

a visual detector having a field of view encompassing said projection surface for detecting a characteristic of an appendage of an operator on said projection surface selected from the group of characteristics consisting of a position of said appendage relative to said surface structure and a movement of said appendage relative to said surface structure, said detector generating a detector output dependent on said characteristic of said appendage; and control means, supplied with said detector output, for identifying a control instruction associated with said characteristic of said appendage and for controlling said at least one of said system components according to said control instruction.

2. A medical system as claimed in claim 1 wherein said control instruction comprises a first control instruction, and said medical system further comprising a displaceable control element simulation mounted on said projection surface and displaceable by said operator, and wherein said visual detector detects displacement of said control element simulation and wherein said detector output is additionally dependent on said displacement of said control element simulation, and wherein said control means comprises means for identifying a second control instruction associated with said displacement of said control element simulation, for controlling said at least one of said system components according to said first control instruction and said second control instruction.

3. A medical system as claimed in claim 2 wherein said visual detector additionally detects gestures of said operator and wherein said detector output is additionally dependent on said gestures, and wherein said control means comprises means for identifying a third control instruction associated with said gestures and for controlling said at least one of said system components according to said first, second and third control instructions.

4. A medical system as claimed in claim 3 wherein said gestures have respective amplitudes associated therewith, and wherein said detector output is additionally dependent on said amplitudes of said gestures.

5. A medical system as claimed in claim 3 wherein said visual detector has a field of view which additionally encompasses a head of said operator, and wherein said visual detector additional detects head movements of said operator and wherein said detector output is additionally dependent on said head movements, and wherein said control means comprises means for identifying a fourth control instruction associated with said head movements and for controlling said at least one of said system components according to said first, second, third and fourth control instructions.

6. A medical system as claimed in claim 5 wherein said visual detector detects a facial expression of said operator and wherein said detector output is additionally dependent on said facial expression, and wherein said control means comprises means for identifying a fifth control instruction association with said facial expression for controlling said at least one of said system components according to said first, second, third, fourth and fifth instructions.

7. A medical system as claimed in claim 6 wherein said control means comprises means for checking whether a combination of said first, second, third, fourth and fifth control instructions would produce an impermissible operation of said at least one of said system components, and for disenabling control of said at least one of said system components if said combination of said first, second, third, fourth and fifth control instructions would produce said impermissible operation.

8. A medical system as claimed in claim 2 wherein said control means comprises means for checking whether a combination of said first and second control instruction would produce an impermissible operation of said at least one of said system components, and for disenabling control of said at least one of said system components if said combination of said first and second control instructions would produce said impermissible operation.

9. A medical system as claimed in claim 1 wherein said control instruction comprises a first control instruction, and wherein said visual detector additionally detects gestures of said operator, and wherein said detector output is additionally dependent on said gestures, and wherein said control means comprises means for identifying a second control instruction associated with said gestures and for controlling said at least one of said system components according to said first and second control instructions.

10. A medical system as claimed in claim 9 wherein said gestures have respective amplitudes associated therewith, and wherein said detector output is additionally dependent on said amplitudes of said gestures.

11. A medical system as claimed in claim 9 wherein said control means comprises means for checking whether a combination of said first and second control instructions would produce an impermissible operation of said at least one of said system components, and for disenabling control of said at least one of said system components if said combination of said first and second control instructions would produce said impermissible operation.

12. A medical system as claimed in claim 1 wherein said control instruction comprises a first control instruction and wherein said visual detector has a field of view encompassing a head of said operator and wherein said visual detector detects a head movement of said operator and wherein said detector output is additionally dependent on said head movement, and wherein said control means comprises means for identifying a second control instruction associated with said head movement for controlling said at least one of said system components according to said first and second control instructions.

13. A medical system as claimed in claim 12 wherein said control means comprises means for checking whether a combination of said first and second control instructions would produce an impermissible operation of said at least one of said system components, and for disenabling control of said at least one of said system components if said combination of said first and second control instructions would produce said impermissible operation.

14. A medical system as claimed in claim 1 wherein control instruction comprises a first control instruction, and wherein said visual detector has a field of view which encompasses a face of said operator, and wherein said visual detector detects a facial expression of said operator and wherein said detector output is additionally dependent on said facial expression, and wherein said control means comprises means for identifying a second control instruction associated with said facial expression for controlling said at least one of said system components according to said first and second control instructions.

15. A medical system as claimed in claim 14 wherein said control means comprises means for checking whether a combination of said first and second control instructions would produce an impermissible operation of said at least one of said system components, and for disenabling control of said at least one of said system components if said combination of said first and second control instructions would produce said impermissible operation.

16. A medical system as claimed in claim 1 wherein said projection surface comprises a first projection surface, and said medical system further comprising a plurality of additional projection surfaces, said first projection surface and said plurality of additional projection surfaces comprising a group of projection surfaces.

17. A medical system as claimed in claim 16 comprising means for selectively projecting said image of at least one operating element on only a selected one of said projection surfaces in said group of projection surfaces or on selected multiple ones of said projection surfaces in said group of projection surfaces.

18. A medical system as claimed in claim 1 further comprising mounting means for said projection surface for selectively orienting said projection surface relative to said operator.

19. A medical system as claimed in claim 1 further comprising means for mounting said projection surface on one of said system components for allowing displacement of said projection surface relative to said one of said system components.

20. A medical system as claimed in claim 1 wherein at least one of said system components generates imaging information, and wherein said imaging information is supplied to said projector and wherein said projector projects said imaging information onto said projection surface.

21. A medical system as claimed in claim 1 wherein at least one of said system components generates system data and wherein said system data are supplied to said projector and wherein said projector projects alphanumeric characters representing said system data on said projection surface.

22. A medical system as claimed in claim 1 wherein said plurality of controllable system components comprise a magnetic resonance imaging apparatus.

23. A medical system as claimed in claim 1 wherein said plurality of controllable system components comprise an X-ray apparatus for producing X-ray shadowgraphs.

24. A medical system as claimed in claim 1 wherein said plurality of controllable system components comprise an ultrasound diagnostic apparatus.

25. A medical system as claimed in claim 1 wherein said plurality of controllable system components comprise an X-ray computed tomography apparatus.

26. A medical system as claimed in claim 25 wherein one of said controllable system components comprises a gantry, and wherein said projection surface is mounted on said gantry.

27. A medical system as claimed in claim 26 wherein said controllable system component comprising said gantry further comprises lateral supports for said gantry, and wherein said projection surface is disposed on one of said lateral supports.

28. A medical system comprising:
a plurality of controllable system components;
a displaceable operating element simulation which simulates an operating element for at least one of said system components and which is displaceable by an operator;
a visual detector having a field of view which encompasses said operating element simulation for detecting displacement of said operating element simulation, said visual detector generating a detector output dependent on said displacement; and
control means, supplied with said detector output, for identifying a control instruction associated with said displacement and for controlling said at least one system component according to said control instruction.

29. A medical system as claimed in claim 28 further comprising:
a projection surface on which said displaceable operating element simulation is disposed;
a projector which projects an image of at least one operating element for at least one of said system components onto said projection surface with said image of said at least one operating element coinciding with said displaceable operating element simulation and wherein said visual detector detects a characteristic of an appendage of said operator on said projection surface selected from the group of characteristics consisting of a position of said appendage relative to said operating element simulation and a motion of said appendage relative to said operating element simulation, and wherein said detector output is additionally dependent on said characteristic of said appendage, and wherein said control instruction comprises a first control instruction and said control means comprises means for identifying a second control instruction associated with said characteristic of said appendage for controlling said at least one of said system components according to said first and second control instructions.

30. A medical system as claimed in claim 29 wherein said projection surface comprises a first projection surface, and said medical system further comprising a plurality of additional projection surfaces, said first projection surface and said plurality of additional projection surfaces comprising a group of projection surfaces.

31. A medical system as claimed in claim 30 comprising means for selectively projecting said image of at least one operating element on only a selected one of said projection surfaces in said group of projection surfaces or on selected multiple ones of said projection surfaces in said group of projection surfaces.

32. A medical system as claimed in claim 29 further comprising mounting means for said projection surface for selectively orienting said projection surface relative to said operator.

33. A medical system as claimed in claim 29 further comprising means for mounting said projection surface on one of said system components for allowing displacement of said projection surface relative to said one of said system components.

34. A medical system as claimed in claim 29 wherein at least one of said system components generates imaging information, and wherein said imaging information is supplied to said projector and wherein said projector projects said imaging information onto said projection surface.

35. A medical system as claimed in claim 29 wherein at least one of said system components generates system data and wherein said system data are supplied to said projector and wherein said projector projects alphanumeric characters representing said system data on said projection surface.

36. A medical system as claimed in claim 29 wherein said plurality of controllable system components comprise an X-ray computed tomography apparatus and wherein one of said controllable system components comprises a gantry, and wherein said projection surface is mounted on said gantry.

37. A medical system as claimed in claim 36 wherein said controllable system component comprising said gantry further comprises lateral supports for said gantry, and wherein said projection surface is disposed on one of said lateral supports.

38. A medical system as claimed in claim 28 wherein said control instruction comprises a first control instruction, and wherein said visual detector additionally detects gestures of said operator, and wherein said detector output is additionally dependent on said gestures, and wherein said control means comprises means for identifying a second control instruction associated with said gestures and for controlling said at least one of said system components according to said first and second control instructions.

39. A medical system as claimed in claim 38 wherein said gestures have respective amplitudes associated therewith, and wherein said detector output is additionally dependent on said amplitudes of said gestures.

40. A medical system as claimed in claim 38 wherein said control means comprises means for checking whether a combination of said first and second control instructions would produce an impermissible operation of said at least one of said system components, and for disenabling control of said at least one of said system components if said combination of said first and second control instructions would produce said impermissible operation.

41. A medical system as claimed in claim 28 wherein said control instruction comprises a first control instruction and wherein said visual detector has a field of view encompassing a head of said operator and wherein said visual detector detects a head movement of said operator and wherein said detector output is additionally dependent on said head movement, and wherein said control means comprises means for identifying a second control instruction associated with said head movement for controlling said at least one of said system components according to said first and second control instructions.

42. A medical system as claimed in claim 41 wherein said control means comprises means for checking whether a combination of said first and second control instruction would produce an impermissible operation of said at least one of said system components, and for disenabling control of said at least one of said system components if said combination of said first and second control instructions would produce said impermissible operation.

43. A medical system as claimed in claim 28 wherein control instruction comprises a first control instruction, and wherein said visual detector has a field of view which encompasses a face of said operator, and wherein said visual detector detects a facial expression of said operator and wherein said detector output is additionally dependent on said facial expression, and wherein said control means comprises means for identifying a second control instruction associated with said facial expression for controlling said at least one of said system components according to said first and second control instructions.

44. A medical system as claimed in claim 43 wherein said control means comprises means for checking whether a combination of said first and second control instruction would produce an impermissible operation of said at least one of said system components, and for disenabling control of said at least one of said system components if said combination of said first and second control instructions would produce said impermissible operation.

45. A medical system as claimed in claim 28 wherein said plurality of controllable system components comprise a magnetic resonance imaging apparatus.

46. A medical system as claimed in claim 28 wherein said plurality of controllable system components comprise an X-ray apparatus for producing X-ray shadowgraphs.

47. A medical system as claimed in claim 28 wherein said plurality of controllable system components comprise an ultrasound diagnostic apparatus.

48. A medical system as claimed in claim 28 wherein said plurality of controllable system components comprise an X-ray computed tomography apparatus.

49. An X-ray computed tomography apparatus comprising:

a plurality of controllable system components including a tiltable gantry mounted on a pair of lateral supports;

a projection surface mounted on one of said lateral supports;

a projector which projects an image of at least one operating element for at least one of said system components onto said projection surface;

said projection surface having at least one surface structure and said projector projecting said at least one image of an operating element onto said at least one surface structure;

a visual detector having a field of view encompassing said projection surface for detecting a characteristic of an appendage of an operator on said projection surface selected from the group of characteristics consisting of a position of said appendage relative to said surface structure and a movement of said appendage relative to said surface structure, said detector generating a detector output dependent on said characteristic of said appendage; and control means, supplied with said detector output, for identifying a control instruction associated with said characteristic of said appendage and for controlling said at least one of said system components according to said control instruction.

50. A computed tomography apparatus as claimed in claim 49 further comprising at least one additional projection surface mounted on said gantry, and wherein said projector comprises means for selectively projecting said image of at least one operating element on a selected one of said projection surface and said additional projection surface, or on both of said projection surface and said additional projection surface.

51. A computed tomography apparatus as claimed in claim 49 wherein at least one of said system components generates system information, and wherein said system information is supplied to said projector and wherein said projector projects said system information onto said projection surface in addition to said image of said at least one operating element.

52. A computed tomography apparatus as claimed in claim 49 wherein at least one of said system components produces an image of a patient, and wherein said image of said patient is supplied to said projector, and wherein said projector projects said image of said patient onto said projection surface in addition to said image of said at least one operating element.

53. A computed tomography apparatus as claimed in claim 49 wherein one of said system components produces a text field, and wherein said text field is supplied to said projector and wherein said projector projects said text field onto said projection surface in addition to said image of said at least one operating element.

54. A medical system as claimed in claim 1 wherein said plurality of controllable system components comprise a nuclear diagnostic apparatus.

55. A medical system as claimed in claim 28 wherein said plurality of controllable system components comprise a nuclear diagnostic apparatus.

* * * * *